United States Patent [19]

Prisell et al.

[11] Patent Number: 5,470,829
[45] Date of Patent: Nov. 28, 1995

[54] PHARMACEUTICAL PREPARATION

[76] Inventors: Per Prisell, Wollmar Yxkullsgatan 15A, S-116 50 Stockholm; Gunnar Norstedt, Foerfattavaegen 46, S-116 42 Bromma, both of Sweden

[21] Appl. No.: 37,124

[22] Filed: Mar. 25, 1993

Related U.S. Application Data

[63] Continuation-in-part of Ser. No. 690,898, Jun. 22, 1990, abandoned.

[30] Foreign Application Priority Data

Nov. 17, 1988 [SE] Sweden .................................. 8804164

[51] Int. Cl.⁶ .......................... A61K 38/00; A61K 45/05; C08G 63/91; C08G 63/48
[52] U.S. Cl. .................................. 514/12; 514/8; 514/21; 514/2; 525/54.1; 424/85.1
[58] Field of Search .................................. 514/12, 8, 23; 424/78, 85.1, 78.01–78.05; 525/54.1

[56] References Cited

U.S. PATENT DOCUMENTS

| | | | |
|---|---|---|---|
| 4,469,681 | 9/1984 | Brownlee | 424/178 |
| 4,636,424 | 1/1987 | Balazs | 514/781 |
| 4,828,563 | 5/1989 | Müller–Lierheim | 424/422 |
| 4,957,744 | 9/1990 | della Valle | 514/5 |
| 4,992,378 | 2/1991 | Kelly | 435/172.3 |
| 5,252,713 | 10/1993 | Morgan, Jr. et al. | 530/391 |

FOREIGN PATENT DOCUMENTS 0224987  6/1987  European Pat. Off. .

OTHER PUBLICATIONS

Schell—Fredrick et al., Eur J. Haematol. vol. 43 p. 286 (1989)–abst. only.
Sprvgel et al., Am . J. Pathol. vol. 179 p. 601 (1987)–abst. only.
Petty et al., Ann. Neurol. vol. 36 p. 244 (1994) abst. only.
Physicians Desk Reference 1994 pp. 504, 815.
R. G. Elgin et al., *Pro. Natl. Acad. Sci.*, 84, 3254–3258, 1987.
Japanese Abstract JO 3063–299–A, Mar. 19, 1991.
Baxter, *Comp. Biochem. Physical.* vol. 91B, 229–235, 1988, Printed in Great Britian.

*Primary Examiner*—Jill Warden
*Assistant Examiner*—Sheela J. Huff
*Attorney, Agent, or Firm*—Browdy and Neimark

[57] ABSTRACT

Pharmaceutical compositions which release the active ingredient slowly are based upon a growth factor or hormone as active ingredient and a means for effecting slow release of the active ingredient. Means for effecting slow release of the active ingredient comprise a conjugate or mixture of a first component and a second component. The first component is a protein other than the active ingredient for binding growth factors and hormones, and the second component is a biodegradable carrier.

9 Claims, No Drawings

PHARMACEUTICAL PREPARATION

CROSS-REFERENCE TO RELATED APPLICATION

The present invention is a continuation-in-part of application Ser. No. 07/690,898, filed Jun. 22, 1990, now abandoned, the entire contents of which are incorporated herein by reference.

BACKGROUND OF THE INVENTION

1. Field of the Invention

The present invention relates to a pharmaceutical preparation comprising at least one receptor/binding protein and a biodegradable polymer, such as hyaluronic acid or a derivative thereof in combination with at least one ligand for the binding proteins.

Using the combination of carrier+receptor/binding protein+active peptide, a slow release preparation is obtained. Alternatively, the principles of the present invention are also useful in controlling abnormally increased production of growth factors, as by tumor growth. In this case, the carrier+receptor/binding protein acts as a selective resorption agent of growth factors.

Receptors are protein molecules that can bind hormones and growth factors, i.e., ligands. Each type of receptor is specific for its ligand. The function of the receptor is to convey external signals, e.g., hormonal signals to the target cell. In addition, the soluble forms of the receptors may have an inherent targeting function which is useful for selective delivery of drugs, such as to injured areas. New achievements in receptor research have made it possible to obtain large quantities of specific pure receptor protein, which makes the present invention possible. Some of the known receptors include insulin-like growth factor-1-receptor, insulin-like growth factor-2-receptor, insulin-receptor, platelet derived growth factor receptor, fibroblast growth factor receptor, colony stimulating factor receptor, transforming growth factor receptors, growth hormone receptor, parathyroid hormone receptor, calcitonin receptor, estrogen receptor, tumor necrosis factor receptor, insulin-like growth factor serum binding protein, erythropoietin receptor and corticosteroid binding globulin.

It is generally known that growth factors and hormones, both in animals and in humans, stimulate important cellular processes concerning cell division, growth, maturation, differentiation, and the like. In addition, healing and regenerative processes are also regulated by these factors. The growth factors/hormones comprise, for example, insulin-like growth factor-1 and -2, IGF-1, IGF-2, platelet derived growth factor, PDGF; epidermal growth factor, EGF; fibroblast growth factor, FGF; nerve growth factor, NGF; colony stimulating factor, CSF; transforming growth factor, TGF; tumor necrosis factor, TNF; calcitonin, CT; parathyroid hormone, PTH; growth hormone, GH; estrogens, bombesin, bone morphogenetic protein, BMP; insulin, erythropoietin and corticosteroids.

Insulin, estrogens, corticosteroids, CT and GH are all well known pharmaceutical agents in daily clinical practice. Research is intense concerning the other different previously mentioned growth factors and hormones. Results of various studies have shown that PDGF and IGF-1 potentiate wound healing, GH increases fracture healing, etc. Although most of these growth factors and hormones have interesting effects, clinical implications for many of them are yet to be found. The results as hitherto obtained indicate that the means of administration currently used restrict the use of the substances as drugs because of the short half-life of peptides, the potency and the potential toxicity of the substances.

2. Description of Related Art

A number of researchers have identified and/or prepared receptors for growth factors or hormones. A partial listing of articles describing these techniques is as follows:

Ullrich, "Insulin-like Growth Factor 1 Receptor cDNA Cloning", *Methods Enzymol.* 1991, 198 p. 17–26.

MacDonald et al., "A Single Receptor Binds both Insulin-like Growth Factor II and Mannose-6-phosphate", *Science,* 1988 239(4844), p. 1134–7.

Paul et al., "Baculovirus-directed Expression of the Human Insulin Receptor and an Insulin-binding Ectodomain", *J. Biol Chem,* 1990, 265(22), p. 13074–83.

Duan et al., "A Functional Soluble Extracellular Region of the Platelet-derived Growth Factor", *J. Biol Chem* 1991, 266(1), p. 413–8.

Kiefer et al., "The Molecular Biology of Heparan Sulfate Fibroblast Growth Factor Receptors", *Ann NY Acad Sci,* 1991 638, p. 167–76.

Perch et al., "A Truncated, Secreted Form of the Epidermal Growth Factor Receptor is Encoded by Alternatively Spliced Transcript in Normal Rat Tissue", *Mol Cell Biol,* 1990, 10 (6), p. 2973–82.

Vissavajjhala et al., "Purification and Characterization of the Recombinant Extracellular Domain of Human Nerve Growth Factor Receptor Expressed in a Baculovirus System", *J. Biol Chem* 1990, 265 (8), p.4746–52.

Rapoport et al., "Granulocyte-macrophage Colony-stimulating Factor (GM-CSF) and Granulocyte Colony-stimulating Factor (G-CSF) Receptor Biology, Signals Transduction and Neutrophil Activation", *Blood Rev,* 1992, 6(1), p. 43–57.

Wang et al.,"Expression Cloning and Characterization of the TGF-beta Type III Receptor", *Cell,* 1991, 67 (4), p. 797–805.

Fuh et al., "Rational Design of Potent Antagonists of the Human Growth Hormone Receptor", *Science,* 1992 256, p. 1677.

Abou-Samra et al., "Expression Cloning of a Common Receptor for Parathyroid Hormone and Parathyroid Hormone-related Peptide from Rat Osteoblast-like Cells: A Single Receptor Stimulates Intracellular Accumulation of both cAMP and Inositol Trisphosphates addn Increases Intracellular Free Calcium", *Proc Natl Acad Sci* USA, 1992, 89(7), p. 2732–6.

Lin et al., "Expression Cloning of an Adenylate Cyclase-coupled Calcitonin Receptor", *Science,* 1991, 254(5034), p. 1022–4.

Brown et al., "Human Estrogen Receptor Forms Multiple Protein-DNA Complexes", *J Biol Chem,* 1990, 265 (19), p. 11238–43.

Himmler et al., "Molecular Cloning and Expression of Human and Rat Tumor Necrosis Factor Receptor Chain (p60) and its Soluble Derivative, Tumor Necrosis Factor-binding Protein", *DNA Cell Biol,* 1990, 9(10), p. 705–15.

Kiefer et al., "Molecular Cloning of a New Human Insulin-like Growth Factor Binding Protein", *Biochem Biophys Res Commun,* 1991, 176(1) p. 219–25.

Ghose-Dastidar et al., "Expression of Biologically Active Human Corticosteroid Binding Globulin by Insect Cells; Acquisition of Function Requires Glycosylation and Transport", *Proc Natl Acad Sci* USA, 1991 88 (5) p. 6408–12.

SUMMARY OF THE INVENTION

The present invention provides a composition for effecting slow release of important peptides while preserving the bioactivity of the peptides. The peptides are connected to carrier materials. In fact, carriers such as hyaluronic acid have beneficial biological effects in themselves, and, for example, a polylactide rod, in addition to being the stabilizing osteosynthetic material, may also act as a slow release carrier, distributing factor healing polypeptides to regions in the body where they are most beneficial.

The present invention thus involves three components: carriers, receptors and ligands. The carriers and receptors together constitute the adjuvant for the active compounds, and the ligands comprise the active compounds. Knowledge of each of these components is extensive; for textbook information, attention is directed to chapters 12 and 14 of Alberts et al., *The Molecular Biology of the Cell*, Garland Publishers, Inc., New York and London, 1989. Based upon its information, it is clear that slow release occurs for the peptides described above if they are administered in a pharmaceutical preparation according to the present invention.

Crosslinking between a matrix gel such as hyaluronic acid and a receptor protein can be achieved by a variety of means. Among these means are crosslinking via imidocarbonates, carbonates, oxiranes, aziridine and activated double bonds and halogens. These strategies have previously been used to immobilize enzymes on polysaccharide gels, and are well known to those skilled in the art.

By definition, a hormone or growth factor-receptor specifically binds its ligand by high affinity and in a reversible manner; the rate of association is much greater than the rate of dissociation. These characteristics of receptors, including high affinity, high specificity and reversibility, are required in order to characterize the entity as a receptor. The dissociation rate is usually determined by incubating the receptor with radiolabelled ligands until equilibrium is reached. Excess unlabelled ligand is added, and the release of non-receptor bound radioactivity measured as a function of time reveals the dissociation rate. From the above information, then, it should be clear that the combination of a carrier with a receptor with a ligand gives, as a generally accepted principle, a slow release of the ligand.

The present invention introduces receptors and defines slow release carriers.

DESCRIPTION OF THE PREFERRED EMBODIMENTS

The slow release pharmaceutical compositions of the present invention thus comprise a ligand which is a growth factor or hormone, a receptor for the growth factor or hormone, and a slow release carrier. That is, the active ingredient is a growth factor or hormone, and the adjuvant which provides the slow release characteristics for the composition is a combination of a receptor for the ligand and a biodegradable carrier. The ligand is conjugated to the receptor for the ligand, and the receptor is in turn bound to the carrier.

Examples of receptors that can be used to prepare the compositions of the present invention are the following:

Erythropoietin-receptor
Insulin-like growth factor-1-receptor
Insulin-like growth factor-2-receptor
Insulin-receptor
Platelet-derived growth factor receptor;
Fibroblast growth factor-receptor
Epidermal growth factor-receptor
Nerve growth factor-receptor
Colony stimulating factor-receptor
Transforming growth factor-receptor
Growth hormone-receptor
Parathyroid hormone-receptor
Calcitonin-receptor
Estrogen-receptor
Tumor necrosis factor-receptor
Insulin-like growth factor serum binding protein
Corticosteroid binding globulin.

Examples of ligands that can be incorporated in compositions according to the present invention to provide slow release of the ligands in vivo are:

Insulin-like growth factor-1
Insulin-like growth factor-2
Platelet-derived growth factor
Epidermal growth factor
Erythroprotein
Fibroblast growth factor
Nerve growth factor
Colony stimulating factor
Transforming growth factor
Tumor necrosis factor
Calcitonin
Parathyroid hormone
Growth hormone
Estrogens
Bombesin
Bone morphogenic protein
Corticosteroids
Insulin Examples of biodegradable polymers which can be used in the present invention are listed below:

Polyglycolide (PGA)
Copolymers of glycolide
Glycolide/L-lactide copolymers (PGA/PLLA)
Glycolide/trimethylene carbonate copolymers (PGA/TMC)
Polylactides (PLA)
Stereo-copolymers of PLA
Poly-L-lactide (PLLA)
Poly-DL-lactide (PDLLA)
L-lactide/DL-lactide copolymers
Copolymers of PLA
Lactide/tetramethylglycolide copolymers
Lactide/trimethylene carbonate copolymers
Lactide/α-valerolactone copolymers
Lactide/ε-caprolactone copolymers
Hyaluronic acid and its derivatives
Polydepsipeptides
PLA/polyethylene oxide copolymers
Unsymmetrical 3,6-substituted poly-1,4-dioxane-2,5-diones
Poly-βhydroxybutyrate (PHBA)
PHBA/β-hydroxyvalerate copolymers (PHBA/HVA)

Poly-p-dioxanone (PDS)
Poly-α-valerolactone
Poly-ε-caprolactone
Methylmethacrylate-N-vinyl pyrrolidine copolymers
Polyesteramides
Polyesters of oxalic acid
Polydihydropyranes
Polyalkyl-2-cyanoacrylates
Polyurethanes (PU)
Polyvinylalcohol (PVA)
Polypeptides
Poly-β-malic acid (PMLA)
Poly-β-alcanoic acids
Alginates.

Preparation of a Slow Release GH-complex

The extracellular domain of the GH receptor was isolated using part of GH receptor cDNA in an expression vector driven by the MT promoter. Purification of this truncated receptor from media of transfected cells was achieved by affinity chromatography on hGH Sepharose (R), followed by a gel chromatographic separation by size.

Commercially available hyaluronic acid was linked to the purified receptor by use of a crosslinking agent as defined above. The high molecular weight complex was purified from the remaining GH receptor by repeated centrifugations. Around 75% of crosslinked receptor was functionally intact.

The crosslinked GH-hyaluronic acid receptor preparation was then incubated with excess levels of GH for two hours at 37° C. and unbound hormone was removed by centrifugation.

The preparation, when injected subcutaneously, slowly released GH in a dose dependent way, based upon the amount of GH and also based upon the number of GH-receptors coupled to the gel. The rate of dissociation for a given preparation is determined for each batch by testing the release of immunoreactive GH in vitro or by testing the release of radioactive GH in animal models.

An experiment measuring the increased body weight subsequent to different types of GH-treatment in a group of hypophysectomized (HX) rats was performed. Three HX rats were subcutaneously injected each with a hyaluronic acid-GH-receptor-GH preparation, according to the present invention, containing approximately 1.2 mg of GH bound to receptor. Three HX rats were subcutaneously injected with the same amount of GH in a water solution, which served as a control. The slow release treated group had significantly increased body weight, lasting more than four days, as compared to the controls.

Examples of biodegradable polymers which can be used in the present invention are listed below:
Hyaluronic acid and its derivatives
Polyglycolide (PGA)
Copolymers of glycolide
Glycolide/L-lactide copolymers (PGA/PLLA)
Glycolide/trimethylene carbonate copolymers (PGA/TMC)
Polylactides (PLA)
Stereo-copolymers of PLA
Poly-L-lactide (PLLA)
Poly-DL-lactide (PDLLA)
L-lactide/DL-lactide copolymers
Copolymers of PLA
Lactide/tetramethylglycolide copolymers
Lactide/trimethylene carbone copolymers
Lactide/α-valerolactone copolymers
Lactide/ε-caprolactone copolymers
Polydepsipeptides
PLA/polyethylene oxide copolymers
Unsymmetrical 3,6-substituted poly-1,4-dioxane-2,5-diones
Poly-βhydroxybutyrate (PHBA)
PHBA/β-hydroxyvalerate copolymers (PHBA/HVA)
Poly-p-dioxanone (PDS)
Poly-α-valerolactone
Poly-ε-caprolactone
Methylmethacrylate-N-vinyl pyrrolidine copolymers
Polyesteramides
Polyesters of oxalic acid
Polydihydropyranes
Polyalkyl-2-cyanoacrylates
Polyurethanes (PU)
Polyvinylalcohol (PVA)
Polypeptides
Poly-β-malic acid (PMLA)
Poly-β-alcanoic acids
Alginates.

All of the above polymers are degraded in the body by hydrolysis. The different polymers vary in their structural and chemical aspects, which afford them differences in strength, action, degradation time, and utility. It is understood that hyaluronic acid derivatives used in the present invention are biodegradable derivatives. PDS, for example, is used as a resorptive suture material. PGA is used in osteosynthetic material such as rods, plates, and screws, as in Biofix(R). PLLA ligaments are used in research as replacement of the anterior cruciate ligament of the knee, etc.

The carriers can be combined as desired, to take advantage of the varying properties of each polymers. For example, the stabilizing osteosynthetic material can be combined with a local slow release of, for example, fracture healing promoting peptides. The biodegradable polymers are structurally porous and having different grades of coating, which facilitates the absorption of the growth factor+receptor complex.

In another experiment, PGA rods of 1.5×8 mm were loaded with radiolabelled IGF-1+ IGF-1 binding protein using vacuum. The end parts of the rods were sealed by melting. The rods were implanted in the end of the tail in three rats. Three control rats were injected in the same part of the tail using the same amount of radiolabelled IGF-1 in a water solution. The rats injected with the slow release composition of the present invention had a significantly higher radioactivity in the tails compared to the controls.

The carriers of the present invention are generally commercially available. For example, hyaluronic acid can be purchased from either Kabi Pharmacia, Sweden, or Biomatrix, USA. Hyaluronic acid can be prepared by the method shown in U.S. Pat. No. 4,141,973.

Ligands for use in the present invention are commercially available from companies such as Sigma Chemical Co. and Genentech, USA; KabiPharmacia Sweden; UCB, Belgium; UBI, USA; Synergen, Boulder, Colo. Alternatively, a skilled molecular biologist can manufacture these proteins by isolating cDNA for the protein of interest and expressing this in prokaryotic or eukaryotic cells.

Receptor-binding proteins are commercially available from a variety of sources. For example, EGF receptor can be obtained from Promega, Inc., USA. Receptor cDNA can alternatively be obtained, as the sequences of these cDNA's are readily obtained by polymerase chain reaction techniques, after which recombinant proteins can be produced as desired.

A number of references are cited as to obtaining essential receptor/binding protein starting materials. Expression of cDNA is the most effective way to obtain large quantities of receptors. However, conventional purification processes are also convenient ways of obtaining these proteins.

Tumor necrosis factor receptor has been cloned by Gray et al., "Cloning of Human Tumor Necrosis Factor (TNF) Receptor cDNA and Expression of Recombinant Soluble TNF-binding Protein" (*Proc. Nat. Acad. Sci.* 1990,. 87: 7384), as well as Himmler et al., *DNA Cell Biol. Dec.* 1990, 9(10), p. 705–715.

Many of the polymers used as carriers in the present invention are commercially available. Molecular weight ranges are not critical to the practice of the present invention. The only criteria for use of these polymers is their inertness in the body as well as their slow release properties.

The following non-limiting examples illustrate various types of slow release compositions that can be made according to the present invention.

EXAMPLE 1

Radio-labelled IGF-I was mixed with hyaluronic acid and release of IGF-I was determined in vivo either after a subcutaneous injection or in vitro in a diffusion chamber. The results showed that the release of IGF-I dissolved in hyaluronic acid is retarded both in vivo and in vitro compared to a preparation consisting of radioactive IGF-I dissolved in physiological saline. (Prisell et al.; *Int. Journal of Pharmaceutics* 1992, 85, 51–56).

EXAMPLE 2

Radiolabelled IGF-I was mixed with an equimolar concentration of IGF-I binding protein (IGF-I-BP) for subsequent mixing with hyaluronic acid. A comparison was made to a preparation consisting of radiolabelled IGF-I mixed with hyaluronic acid (control). Various concentration of either components were used essentially following the example described by Prisell et al. The test system for in vitro release consisted of diffusion chambers described and referred to in Example 1. The results showed that the addition of IGF-I binding protein resulted in a significantly retarded release of IGF-I compared to control. This was the case over a wide range of IGF-I/IGF-BP concentrations.

EXAMPLE 3

(a) Two groups of rats were injected in the tail by either 6 μg IGF-I+IGF-I binding protein+hyaluronic acid and another group with 6 μg IGF-I in a water solution. The IGF-I as used contained trace amounts (200 000 cpm) of radiolabelled IGF-I. Three rats were analyzed at each occasion. After different points of time the end of the tail was amputated and the radioactivity analyzed. The first group of rats were found to release IGF-I significantly more slowly (more than two days) than the controls.

(b) In an additional experiment using the same ingredients as in Example (3a) another in vivo test using the hind foot of the rat was carried out as described by Prisell et al in *Int. Journal of Pharmaceutics* 1992, 85, 51–56. The preparation containing IGF-I binding protein resulted in a retardation of release compared to the preparation without IGF-I binding protein.

EXAMPLE 4

As described above, preparations were made consisting of either IGF-I+IGF-I binding protein+hyaluronic acid or IGF-I and hyaluronic acid. These preparations were tested in a diffusion chamber allowing diffusion of proteins from a donor compartment into a receiver compartment (described by Prisell et al). The IGF-I in the receiving compartment was tested for bioactivity using a bioassay where the mitogenic effect of IGF-I is tested. It was found that bioactive IGF-I was released from both preparations and that the bioactive IGF-I followed a similar time course as predicted from radioactive IGF-I release as measured in experiment 2.

EXAMPLE 5

Five hundred ng of IGF-I and equimolar amounts of IGF-I binding protein were mixed and slowly allowed to precipitate in a gradient of increasing amounts of acetone. The precipitate was mixed with 0.5 ml of a 10% solution of poly-DL-lactic acid in acetone. The resulting slurry was emulsified with 5 ml of silicone oil and dispersed in a 0.9% solution of sodium chloride in water. The thereby formed micro particles were filtered off and subjected to testing for release of encapsulated material in vitro as well as in vivo. They showed significant slow release properties.

EXAMPLE 6

FGF (1.5 μg) and equimolar amount of a FGF receptor were mixed in 1 ml of a 0.9% solution of sodium chloride in water. The resulting solution was precipitated in a gradient of increasing concentration of acetone. The precipitate was mixed with 0.5 ml of a 10% solution of a 75/25% copolymer of DL lactic/glycolide. Approximately 40 μl of the resulting slurry was deposited in each decalcified bone implant. According to the model of Urist (1965, *Science* 150:893–899) these implants, and control implants with FGF in saline, were deposited subcutaneously in male Sprague-Dawley rats. The slow release FGF+receptor composition induced significantly more bone growth compared to the equivalent amount of FGF in saline among the controls.

EXAMPLE 7

A freeze dried mixture of Erythropoietin (50.000 IU) and equimolar amounts of its extracellular receptor was dispersed in an ethylacetate solution of 5% poly-β-hydroxybutyrate. The mixture was sprayed out in streaming water and filtered off and dried. The resulting powder was formulated into a parenteral solution and injected into mice for further analysis. The release of erythropoietin activity lasted for 14 days.

EXAMPLE 8

A membrane was formed by drying 5 ml of a 5% solution of poly-β-hydroxybutyrate/hydroxyvalerate copolymer in a glass petri dish. A mixture of 0.5 μg of nerve growth factor (NGF) and equimolar amount of Nerve Growth Factor receptor was dried onto the surface of the membrane. The membrane was then folded so that the active surfaces faced to each other. The membrane was then rolled onto a glass rod 2 mm thick. By adding a few drops of chloroform the membrane was glued together to form a tube. The tube was used to connect two ends of the cut Sciatic nerve in male Sprague-Dawley rats at a slow rate according to RIA for NGF performed on into the tube micro injected and aspirated saline.

EXAMPLE 9

One hundred mg of medical grade alginate MVM was dissolved in 5 g of a mixture composed of 500 μg of Calcitonin (CT) receptor and equimolar amounts of radiolabelled Calcitonin (Cibacalcin®) in physiological buffer. About 0.5 ml (i.a. ≈400000 cpm) of this highly viscous mixture was injected in the dorsal part of the hind foot of New Zealand rabbits. Control rabbits were injected with radio-labelled CT in saline. The decline of radioactivity was evaluated using a GM-tube and was estimated to be significantly decreased in the CT+receptor+alginate MVM group compared to controls.

EXAMPLE 10

In a similar experiment as in Example 9, 1 ml radiolabelled Calcitonin (CT) (Cibacalcin®) and equimolar amount of CT receptor was added to freeze-dried Hyaluronan (equivalent to 1 ml of 0.35% Hyaluronan-gel [Biomatrix, USA]). Radiolabelled CT in saline solution was used as a control. In the following experiment approximately 40 μl of either solution was injected in the dorsal part of the hind foot in male Sprague-Dawley rats according to a model described by Prisell et al., *Int. Journal of Pharmaceutics* 1992, 85, 51–56. The decline of radioactivity could be estimated through the aid of a GM-tube, and showed a striking difference between the two groups. The control group declined its local radioactivity in a significant faster way compared to the slow release group.

EXAMPLE 11

Four μg TGFβ1 and equimolar amounts of a TGFβ1 receptor were mixed in 1 ml of a 0.9% solution of sodium chloride in water. The resulting solution was precipitated in a gradient of increasing concentration of acetone. The precipitate was mixed with 0.5 ml of a 10% solution of a 75/25% copolymer of DL lactic/glycolide. Approximately 80 μl of the resulting slurry was injected in close contact with the periosteal layer in male Sprague-Dawley rats' thigh bones. This slow release composition showed a marked periosteal osteoinductive effect compared to an injected control solution containing equivalent amounts of TGFβ1 in saline.

EXAMPLE 12

Alginate dressings (Kaltostat®, CV Laboratories Ltd., UK) approximately 0.5×1 cm large were soaked with radiolabelled EGF+EGF receptor solution. The solution contained 10 μg EGF and an equimolar amount of EGF receptor. The EGF-+receptor-saturated dressing was used to cover a newly created superficial wound on the dorsal proximal part of the tail of male Sprague-Dawley rats. The dressings were kept in place through the aid of a transparent tape (Tegaderm®3M, USA), gently wrapped around the tail covering each dressing and underlying wound. The local radioactivity could be estimated using a GM-tube. The decline by time of local radioactivity was compared to a control group of similarly wounded rats, which wounds also were gently covered by Tegaderm and injected through the Tegaderm with an equivalent amount of radio-labelled EGF in saline. The local radioactivity lasted significantly longer among the rats in the Alginate dressing group.

EXAMPLE 13

A slow release preparation is made by immobilizing on a glycolide/L-lactide copolymer a mixture of insulin-like growth factor-1 receptor and insulin-like growth factor-1. This slow release composition is useful in administering insulin-like growth factor-1 to a patient in need thereof.

EXAMPLE 14

A slow release preparation is made by immobilizing by imidocarbonate crosslinking to alginate erythropoietin and erythropoietin-receptor. This preparation is administered to a patient in need thereof to release slowly erythropoietin over an extended period of time.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. In a method for administering ligand selected from the group consisting of growth factors and hormones to an animal comprising administering said ligand in combination with an adjuvant which controls the release of said ligand, said adjuvant comprising a biodegradable polymer and a receptor for said ligand, wherein said receptor is conjugated to a biodegradable polymer, the improvement wherein said receptor comprises (1) a protein for binding said ligand, said protein being selected from the group consisting of insulin-like growth factor-1-receptor; erythropoietin-receptor; insulin-like growth factor-2-receptor; insulin-receptor; platelet derived growth factor-receptor; fibroblast growth factor-receptor; colony stimulating growth factor-receptor; transforming growth factor-receptor; growth hormone-receptor; parathyroid hormone-receptor; calcitonin-receptor; estrogen-receptor; insulin-like growth factor serum binding protein; epidermal growth factor receptor; corticosteroid binding globulin; and bone morphogenic protein and (2) said biodegradable polymer is selected from the group consisting of alginates; hyaluronic acid and derivatives thereof: polyglycolide; copolymers of glycolide; copolymers of glycolide and L-lactide; copolymers of glycolide and trimethylene carbonate; polylactides; stereo-copolymers of polylactides; poly-L-lactide; poly-DL-lactide; copolymers of L-lactide and DL-lactide; copolymers of polylactide; copolymers of lactide and tetramethylglycolide; copolymers of lactide and trimethylene carbonate; copolymers of lactide and α-valerolactone; copolymers of lactide and ε-caprolactone; copolymers of polylactide and polyethylene oxide; copolymers of poly-β-hydroxybutyrate; polyurethanes; methylmethacrylate-N-vinyl pyrrolidone copolymers;

and poly-p-dioxanone;

said ligand being a ligand specific to said protein and being linked to said protein.

2. The method according to claim 1 wherein said active ingredient is IGF-1.

3. The method according to claim 1 wherein said receptor comprises the extracellular domain of the protein for binding said ligand.

4. The method according to claim 1 wherein the biodegradable polymer is hyaluronic acid.

5. The method according to claim 4 wherein the ligand is IGF-1.

6. A method for administering a pharmaceutical preparation to a patient in need thereof comprising administering to said patient a slow release conjugate comprising as active ingredient a ligand selected from the group consisting of growth factors and hormones in combination with an adjuvant which controls the release of said ligand, said adjuvant selected from the group consisting of receptors for said ligand and binding proteins for said ligand, and a biodegradable polymer as carrier for said slow release conjugate, wherein said biodegradable polymer is selected from the group consisting of alginates; hyaluronic acid and derivatives thereof; polyglycolide; copolymers of glycolide; copolymers of glycolide and L-lactide; copolymers of glycolide and trimethylene carbonate; polylactides; stereo-copolymers of polylactides; poly-L-lactide: poly-DL-lactide; copolymers of L-lactide and DL-lactide; copolymers of polylactide; copolymers of lactide and tetramethylglycolide; copolymers of lactide and trimethylene carbonate; copolymers of lactide and $\alpha$-valerolactone; copolymers of lactide and $\epsilon$-caprolactone; copolymers of polylactide and polyethylene oxide; copolymers of poly-$\beta$-hydroxybutyrate; polyurethanes; methylmethacrylate-N-vinyl pyrrolidone copolymers; and poly-p-dioxanone.

7. The method according to claim 6 wherein said receptor is conjugated to said biodegradable polymer.

8. The method according to claim 6 wherein said ligand is selected from the group consisting of insulin-like growth factor-1; insulin-like growth factor-2; platelet-derived growth factor; epidermal growth factor; erythropoietin; fibroblast growth factor; colony stimulating factor; transforming growth factor; calcitonin; parathyroid hormone; growth hormone; estrogens; bone morphogenic protein; corticosteroids; and insulin.

9. The method according to claim 6 wherein said receptor comprises the extracellular domain of said receptor or said binding protein comprises the extracellular domain of said binding protein.

* * * * *